(12) United States Patent
Mizusawa

(10) Patent No.: US 8,889,262 B2
(45) Date of Patent: Nov. 18, 2014

(54) METHODS AND SYSTEMS FOR DELIVERING WOOD PRESERVATIVES

(75) Inventor: Atsushi Mizusawa, Kyoto (JP)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/878,733

(22) PCT Filed: Jul. 16, 2012

(86) PCT No.: PCT/US2012/046937
§ 371 (c)(1),
(2), (4) Date: Apr. 10, 2013

(87) PCT Pub. No.: WO2014/014445
PCT Pub. Date: Jan. 23, 2014

(65) Prior Publication Data
US 2014/0017506 A1    Jan. 16, 2014

(51) Int. Cl.
*B32B 23/04*    (2006.01)
(52) U.S. Cl.
USPC ........ 428/532; 428/535; 428/536; 428/537.1; 427/397; 516/24; 514/354
(58) Field of Classification Search
USPC ............... 428/532, 535, 536, 537.1; 427/397; 516/24; 514/354
See application file for complete search history.

(56) References Cited

U.S. PATENT DOCUMENTS

| 4,115,313 A * | 9/1978 | Lyon et al. ............ 516/24 |
| 4,532,251 A * | 7/1985 | Spatz ............... 514/354 |
| 5,213,805 A * | 5/1993 | Wallach et al. ........... 424/450 |
| 2005/0255251 A1 * | 11/2005 | Hodge et al. ........... 427/397 |

OTHER PUBLICATIONS

Keffer,J.L. "Motualevic Acids A-F . . . " Organic Letters 2009, 11;1087-1090.*
Vaca-Garcia,C. "Cellulose Esterification with Fatty Acids . . ." Journal of the American Oil Chemists Society, 1998, 75:315-319.*
Keffer, J.L. "Motualevic Acids A-F, Antimicrobial Acids from the Sponge Siliquariaspongia sp." Organic Letters 2009 11:1087-1090.
Vaca-Garcia, C. "Cellulose Esterification with Fatty Acids and Acetic Anhydride in Lithium Chloride/N,N-Dimethylacetamide Medium" Journal of the American Oil Chemists Society 1998 75:315-319.
International Search Report issued on the corresponding PCT Application No. PCT/US 12/46937, dated Sep. 21, 2012.
McCormick, C.L. "Solution Studies of Cellulose in Lithium Chloride and N,N-Dimethylacetamide" Macromolecules 1985 18:2394-2401.

* cited by examiner

*Primary Examiner* — Leszek Kiliman
(74) *Attorney, Agent, or Firm* — Knobbe Martens Olson & Bear LLP

(57) ABSTRACT

The present application relates to wood preservation, for example, surfactants and phospholipids for improving wood preservation. Included are surfactants and phospholipids containing a 2-amino-N,N-dimethylacetamide. Provided are wood preservative compositions containing these surfactants or phospholipids, methods of applying such wood preservative compositions to wood, and wood products resultant from some such methods. Also provided are wood products containing the wood preservative compositions provided herein.

23 Claims, 4 Drawing Sheets

METHODS AND SYSTEMS FOR DELIVERING WOOD PRESERVATIVES

This application is the U.S. National Phase under 35 U.S.C. §371 of International Application No. PCT/US2012/046937, filed Jul. 16, 2012.

BACKGROUND

1. Field

The present application relates to wood preservation, for example, surfactants and phospholipids for improving wood preservation.

2. Description of the Related Art

Lipid soluble or water soluble wood preservatives are commonly used in treating wood. However, such preservatives have problems being taken up into the cells of the wood due to the surface structure of wood cell walls.

Furthermore, traditional wood preservative treatments that remain at the surface of wood cell walls are susceptible to washing away, resulting in a loss of the preservative effect over time.

SUMMARY

Some embodiments disclosed herein include a wood preservative composition comprising a micelle or liposome, wherein the micelle or liposome comprises at least one surfactant that comprises a 2-amino-N,N-dimethylacetamide (DMAc) moiety; and at least one wood preservative compound contained within the micelle or liposome. In some embodiments, the wood preservative composition is in aqueous dispersion form. In some embodiments, the concentration of the wood preservative composition in the aqueous dispersion is about 0.1 µM to about 10 mM. In some embodiments, the wood preservative composition further comprises at least one lithium salt in the aqueous dispersion. In some embodiments, the lithium salt is lithium chloride. In some embodiments, the total amount of lithium salt present in the composition is about 0.1 µM to about 10 mM. In some embodiments, the micelle or liposome further comprises at least one surfactant that does not contain a DMAc moiety. In some embodiments, the wood preservative composition comprises micelles. In some embodiments, the micelles have a mean diameter of about 10 nm to about 50 nm. In some embodiments, the wood preservative compound is lipid surfactant or soap soluble. In some embodiments, the wood preservative compound is sodium dodecyl sulfate, sodium laureth sulfate, cetylpyridinium chloride, polyethoxylated tallow amine, cetyl alcohol, stearyl alcohol or combinations thereof. In some embodiments, the wood preservative composition comprises unilamellar liposomes. In some embodiments, the unilamellar liposomes have a mean diameter of about 30 nm to about 60 nm. In some embodiments, the wood preservative compound is water soluble. In some embodiments, the wood preservative compound is phosphatidylcholines, phosphatidylethanolamine, cholesterol, phosphatidylserine, phosphatidylinositol, or combinations thereof. In some embodiments, the surfactant that comprises a DMAc moiety further comprises a $C_{8-50}$ alkyl moiety. In some embodiments, the surfactant that comprises a DMAc moiety further comprises a phosphatidyl serine moiety. In some embodiments, the surfactant that comprises a DMAc moiety is stearoyl-2-amino-N,N-dimethylacetamide, lauroyl-2-amino-N,N-dimethylacetamide, or a combination thereof. In some embodiments, the amount of surfactant containing a DMAc moiety in the micelle or liposome is about 1% to about 95% (w/w) relative to the total amount of surfactant in the micelle or liposome. In some embodiments, the amount of wood preservative compound contained in the wood preservative composition is about 70% to about 99% (w/w) relative to the total amount of the wood preservative composition.

In some embodiments, provided are wood preservative compositions comprising: at least one surfactant that comprises a 2-amino-N,N-dimethylacetamide (DMAc) moiety; at least one wood preservative compound; and an aqueous solvent. Some embodiments, further comprise at least one lithium salt. In some embodiments, the lithium salt is lithium chloride.

Also provided are preserved wood products comprising a wood product and any of the wood preservative compositions provided herein.

Also provided are methods of preserving wood, the method comprising: providing untreated wood; and applying to the untreated wood any of the wood preservative compositions provided herein. In some embodiments, the wood preservative composition is dispersed in water prior to applying the wood preservative composition to the untreated wood. In some embodiments, the quantity of wood preservative composition applied to the untreated wood is about 10 mg per $cm^2$ of wood surface to about 1 mg per $cm^2$ of wood surface. In some embodiments, the quantity of wood preservative compound applied to the untreated wood is about 100 µg/$cm^2$ to about 10 µg/$cm^2$. In some embodiments, the applying step comprises spraying the wood preservative composition onto the untreated wood. In some embodiments, the wood preservative composition is applied to the untreated wood at a pressure of about 0.1 kg/$cm^2$ to about 2 kg/$cm^2$. Some embodiments further comprise drying the treated wood. In some embodiments, the wood preservative composition is applied to the untreated wood at a temperature of 80° C. or greater. In some embodiments, at least 80% of the wood preservative composition is at least 1 µm below the surface of the treated wood within five hours after the applying step.

Also provided are preserved wood products that have been treated by any of the methods provided herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail, in part through use of the accompanying drawings.

DETAILED DESCRIPTION

Figure 1:
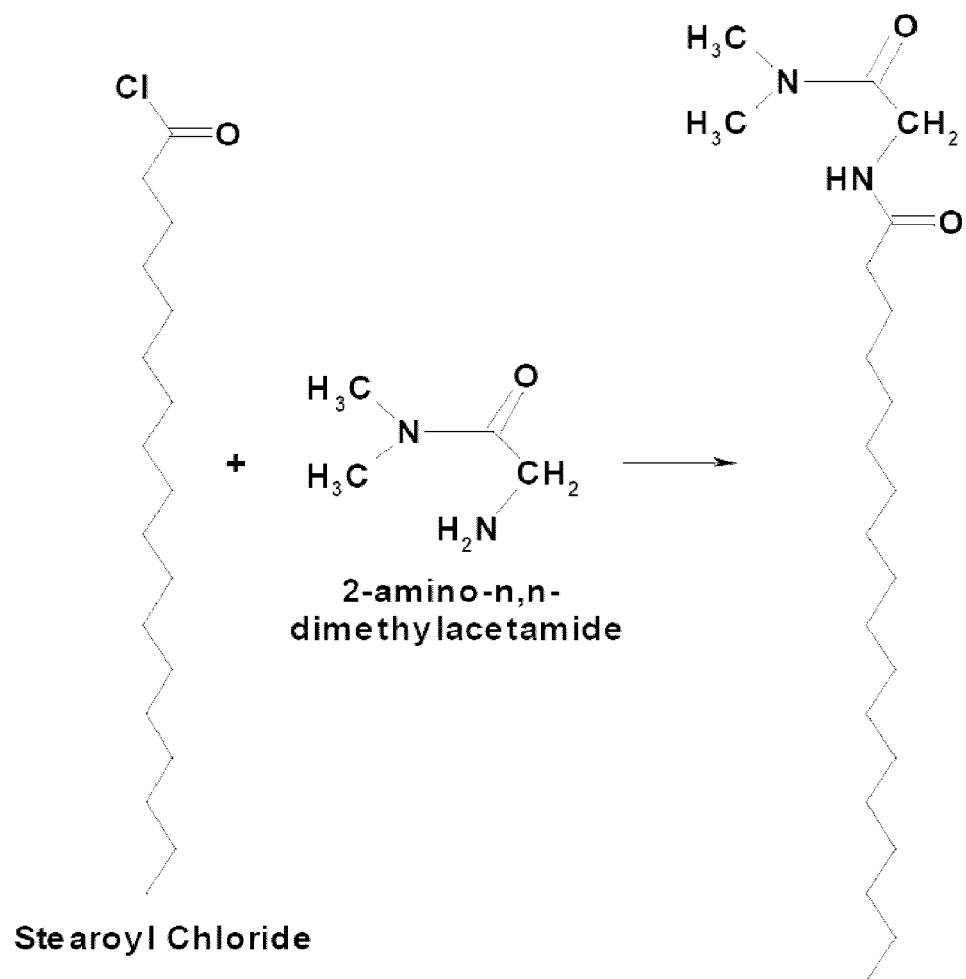
FIG. 1 shows a schematic representation of a surfactant containing a DMAc scaffold that can be used in micelles or liposomes for delivery of wood preservatives, and, aligned with the schematic representation, a non-limiting example compound.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Among the embodiments provided herein are wood preservation compositions comprising a micelle or liposome and at least one wood preservative compound contained within the micelle or liposome. In particular embodiments, the micelle or liposome comprises at least one surfactant or phospholipid that comprises a 2-amino-N,N-dimethylacetamide (DMAc) moiety. In some embodiments, wood preservation compositions are provided comprising at least one surfactant or phospholipid that comprises a DMAc moiety, at least one wood preservative compound, and an aqueous solvent. In some embodiments, the wood preservation compositions are in aqueous dispersion form, where the aqueous dispersion can contain lithium ion. Also provided herein are methods of preserving wood comprising providing untreated wood, and applying to the untreated wood a wood preservative composition in accordance with the wood preservative compositions provided herein.

Various wood preservatives for the purpose of protecting wood materials have been developed in the past. However, highly potent wood preservatives often have a negative impact on human health, and less potent preservatives pose problems with long-term efficacy and durability. A typical problem with traditional preservatives is that, because wood materials have cell walls that are surrounded by tough cellulose, wood preservatives do not permeate the cells, regardless of the type of chemical. Use of potent wood preservative can be hazardous when the preservative does not enter the cell walls and diffuses out through vascular bundles of the wood. However, if wood material preservation treatment is performed by applying pressure or temperature such that the cell wall is destroyed, the strength of the wood materials can be lost.

The compositions and methods provided herein address these issues by introducing preservative into the cells without damaging wood cellulose, and/or by controlled release in which preservative fixed at the surface of the cell walls is gradually released over time. While not intending to be bound by the following theory, it is believed that the wood preservation compositions provided herein can infiltrate the cells, and can release the wood preservative held within due to a difference in osmotic pressure between the inside and outside of the cells. The DMAc moiety can bond with cellulose in plant cell walls together with a salt such as lithium chloride. When the salt concentration is high, the wood preservative composition can infiltrate the plant cells, and when the salt concentration is low, the state in which the wood preservative composition is bonded with cellulose is maintained. If the salt concentration during the wood preservation treatment is lowered, the wood preservative composition does not infiltrate the cells and the wood preservation treatment is completed in a state in which bond between cell walls and the wood preservative composition is maintained. After this, the wood is made available for commercial use, and when a moist state of the wood slowly shifts to a dry state over time, the wood preservative composition eventually releases the wood preservative held inside over a span of years. On the other hand, if microbial invasion or a rapid increase in humidity occurs while slowly shifting to the dry state, the wood preservative composition will release the wood preservative held inside in response to the rapid changes in osmotic pressure. By doing so, the wood preservative composition can be used for controlled release, where preservative inside the wood preservative composition is released in the cases of microbial invasion or abnormal increases in humidity after the completion of preservation treatment.

DEFINITIONS

As used herein, and "DMAc" is a chemical moiety with the structure 2-amino-N,N-dimethylacetamide. In some embodiments, the DMAc moiety is part of a surfactant or phospholipid molecule such as, for example, stearoyl-2-amino-N,N-dimethylacetamide, lauroyl-2-amino-N,N-dimethylacetamide, or 3-(dimethylcarbamoyl)propanoyl phosphatidylserine.

As used herein, "untreated wood" is a wood product that has not been treated to alter the cellulose structure or composition in the pits of the wood product. For example, untreated wood can include a wood product that has not been treated to dissolve the cellulose microfibrils in the pits of the wood product. In some embodiments, the untreated wood used in the methods provided herein includes hardwoods, softwoods, lumber, or other wood for which the goal is the preservation thereof. The untreated wood can generally be of any size and shape. In some embodiments, the largest dimension of a piece of untreated wood used in the methods provided herein is at least or at least about 20, 30, 40, 50, 60, 70, 80, 90 or 100 cm.

As used herein, a "wood preservative composition" is a mixture of two or more different chemical species, where at least one of the chemical species is a wood preservative compound.

As used herein, a "wood preservative compound" is a chemical species that is used in the preservation of wood. Examples of wood preservative compounds include, but are not limited to sodium dodecyl sulfate, sodium laureth sulfate, cetylpyridinium chloride, polyethoxylated tallow amine, cetyl alcohol, stearyl alcohol, phosphatidylcholines, phosphatidylethanolamine, cholesterol, phosphatidylserine, and phosphatidylinositol.

Wood Preservative Composition

In the process of wood preservation, delivery of wood preservative compounds into the cells of wood can provide an effective manner for improved, long-lasting wood preservation. As provided herein, micelles and liposomes can be used as delivery vehicles for delivering the wood preservative compound into wood cells. For example, micelles can be instrumental in delivering lipid-soluble preservatives, and liposomes can be instrumental in delivering water-soluble preservatives.

In some embodiments, provided are wood preservation compositions that contain a micelle or liposome, where the micelle or liposome comprises at least one surfactant or phospholipid that comprises a 2-amino-N,N-dimethylacetamide (DMAc) moiety, and at least one wood preservative compound contained within the micelle or liposome. Without intending to be bound by theory, it is contemplated herein that DMAc structures can form chemical bonds with cellulose, particularly when accompanied by an ion such as lithium chloride. These chemical bonds, when stretched to a sufficient extent, can break hydrogen bonds between cellulose molecules, thereby dissolving cellulose.

In some embodiments, provided is a wood preservative composition comprising at least one surfactant or phospholipid that comprises a 2-amino-N,N-dimethylacetamide (DMAc) moiety; at least one wood preservative compound; and an aqueous solvent. While in some instances a micelle or liposome may be formed, there is no absolute requirement to demonstrate formation of these vesicles in order to achieve the wood preservation effect of the wood preservation compositions provided herein.

DMAc-Containing Compounds

The wood preservation compositions provided herein contain a DMAc moiety incorporated into a surfactant or a phospholipid molecule. For example, a DMAc moiety can be attached to a long chain alkyl carboxylic acid, such as lauric acid or stearic acid, or can be incorporated into a phospholipid such as phosphatidylserine. The molecules into which DMAc is incorporated can possess a polar or hydrophilic region and a separate non-polar or hydrophobic region. When DMAc is incorporated into the molecule, it can in some cases be incorporated into the polar or hydrophilic region of the molecule.

Surfactants containing DMAc moieties can include a long chain alkyl carboxylic acid linked to DMAc via the amine nitrogen of DMAc. Examples of long chain alkyl carboxylic acids that can be linked to DMAc as provided herein include, but are not limited to, $C_{8-50}$ alkyl carboxylic acids, such as $C_{10-20}$ alkyl carboxylic acids, particularly, $C_{12-18}$ alkyl carboxylic acids such as lauric acid, myristic acid, palmitic acid, and stearic acid. DMAc-modified long chain alkyl carboxylic acids can be prepared according to any of a variety of methods known in the art, such as reacting 2-amino-N,N-dimethylacetamide with a long chain alkyl acid chloride such as stearoyl chloride.

The surfactants containing DMAc moieties such as DMAc-modified long chain alkyl carboxylic acids can be incorporated into micelles. The micelles into which the DMAc-modified long chain alkyl carboxylic acids are incorporated can in some cases be characterized by being aggregates of surfactant molecules that are sufficiently large to accommodate one or more DMAc-modified surfactants as well as one or more wood preservative compounds, and can associate with the cellulose of wood. For example, such micelles can in some cases be 10-50 nm in diameter, where, in aqueous solution, the surfactants in the micelles have polar portions on the exterior of the micelle and non-polar portions in the interior of the micelle. The micelles can in some cases contain about 50-200 surfactants per micelle. Surfactants, other than the DMAc-modified surfactants, that can be used in forming the micelles include cationic surfactants, anionic surfactants, zwitterionic surfactants, and non-ionic surfactants, where particular examples of such surfactants include, but are not limited to, lauric acid, myristic acid, palamitic acid, stearic acid, and mixtures thereof. The critical micelle concentration of the non-DMAc containing surfactants can in some cases be about 0.01 µM to about 10 mM.

The amount of DMAc-modified long chain alkyl carboxylic acids incorporated into the micelles can be an amount sufficient to generate affinity between the micelles and plant cell walls under low salt conditions, and/or to permit infiltration of the micelles under high salt conditions. In some examples, the amount of DMAc-modified long chain alkyl carboxylic acids incorporated into the micelles can be at least, at least about, more than, or more than about 5, 10, 15, 20, 25, 30 or 35 mole %, and up to, up to about, less than or less than about 65, 70, 75, 80, 85, 90 or 95 mole %.

Phospholipids containing DMAc moieties can include phosphoglycerides (phospholipids where a phosphate is bonded to a glyceride) and phosphosphingolipids (phospholipids where a phosphate is bonded to a ceramide), where the DMAc moiety can be linked to the phospholipid via a derivitizable moiety in the polar head group of the phospholipid, such as a carboxylate moiety or an amine moiety of the phospholipid. Examples of phospholipids that can be linked to DMAc as provided herein include, but are not limited to, phosphatidylserine, phosphatidylethanolamine, phosphatidic acid and phosphatidylinositol. DMAc-modified phospholipids can be prepared according to any of a variety of methods known in the art, such as forming an acid chloride, such as 3-(dimethylcarbamoyl)propanoic acid chloride, and linking the acid chloride compound to the amino group of a phospholipid such as phosphatydylserine.

The phospholipids containing DMAc moieties such as DMAc-modified phosphoglycerides can be incorporated into liposomes. The liposomes into which the DMAc-modified phospholipids are incorporated can in some cases be characterized as unlilamellar bilayer aggregates of phospholipids that are sufficiently large to accommodate one or more DMAc-modified phospholipids as well as one or more wood preservative compounds, and can associate with the cellulose of wood. For example, such liposomes can be about 30-60 nm in diameter, where, in aqueous solution, the surfactants in the liposomes have polar portions on the external and internal surfaces of the liposome and non-polar portions are in the interior of the lipid bilayer. The liposomes can in some cases contain about 50-200 phospholipids per liposome. Phospholipids, other than the DMAc-modified phospholipids, that can be used in forming the liposomes include phosphoglycerides and phosphosphingolipids, where particular examples of such phospholipids include, but are not limited to, phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, saccharolipids, and mixtures thereof.

The amount of DMAc-modified phospholipids incorporated into the liposomes can be an amount sufficient to generate affinity between the liposomes and plant cell walls under low salt conditions, and/or to permit infiltration of the liposomes under high salt conditions. For example, the amount of DMAc-modified phospholipids incorporated into the micelles can be at least, at least about, more than, or more than about 5, 10, 15, 20, 25, 30 or 35 mole %, and up to, up to about, less than or less than about 65, 70, 75, 80, 85, 90 or 95 mole %.

Wood Preservative Compound

The wood preservative compositions provided herein can contain one or more wood preservative compounds. Any of a variety of wood preservative compounds can be used herein, and the wood preservative compounds can be water soluble, surfactant soluble, or lipid soluble. Examples of lipid soluble or surfactant soluble wood preservative compounds include, but are not limited to sodium dodecyl sulfate, sodium laureth sulfate, cetylpyridinium chloride, polyethoxylated tallow amine, cetyl alcohol, stearyl alcohol, and combinations thereof. Lipid soluble or surfactant soluble wood preservative compounds can be incorporated into a micelle such as the DMAc-modified surfactant-containing micelles described herein above. Examples of water soluble or surfactant soluble wood preservative compounds include, but are not limited to phosphatidylcholines, phosphatidylethanolamine, cholesterol, phosphatidylserine, phosphatidylinositol, and combinations thereof. Water soluble or surfactant soluble wood preservative compounds can be incorporated into a liposome such as the DMAc-modified surfactant-containing liposomes described herein above.

Aqueous Dispersions

In some embodiments, the wood preservative compositions provided herein are in aqueous dispersion form. That is, in some embodiments, the micelles or liposomes that contain a DMAc-modified surfactant or phospholipid and a wood preservative compound are dispersed in an aqueous liquid. In such aqueous dispersions, the concentration of the wood preservative composition in the aqueous dispersion is at least, at least about, greater than, or greater than about 0.1, 0.2, 0.3, 0.4, 0.5, 0.6, 0.7, 0.8, 0.9, 1, 1.2, 1.5, 2, 2.5, 3, 4, 5, 6, 7, 8, 9, 10, 12, 15, 20, 25, 30, 35, 40, 45, 50, 60, 70, 80, 90, 100, 120, 150, 200, 250, 300, 350, 400 or 500 µM, and less than, less than about, up to, or up to about 0.1, 0.12, 0.15, 0.2, 0.25, 0.3, 0.35, 0.4, 0.5, 0.6, 0.7, 0.8, 0.9, 1, 1.2, 1.5, 2, 3, 4, 5, 6, 7, 8, 9 or 10 mM. Expressed in different terms, for aqueous dispersions of micelles containing wood preservative compound, the concentration of aqueous dispersions of micelles containing wood preservative compound in the aqueous dispersion is at least, at least about, greater than, or greater than about 20, 25, 30, 40, 50, 60, 70, 80, 90, 100, 120, 150, 200, 250, 300, 400, 500, 600, 700, 800, 900, 1000, 1200, 1500, 2000, 2500, 3000, 3500, 4000, 4500, 5000, 6000, 7000, 8000, 9000, 10,000, 12,000, 15,000, 20,000, 25,000, 30,000, 35,000, 40,000 or 50,000 µg/L, and less than, less than about, up to, or up to about 2, 2.5, 3, 3.5, 4, 5, 7.5, 10, 15, 20, 25, 30, 50, 75, 100, 200, 300, 400, 500, 700, 1000, 1500, 2000, 2500, 3000 or 3500 mg/L. For aqueous dispersions of liposomes containing wood preservative compound, the concentration of aqueous dispersions of liposomes containing wood preservative compound in the aqueous dispersion is at least, at least about, greater than, or greater than about 50, 75, 100, 150, 200, 250, 300, 350, 400, 450, 500, 700, 1000, 1500, 2000, 2500, 3000, 3500, 4000, 4500, 5000, 6000, 7000, 8000, 9000, 10,000, 12,000, 15,000, 20,000, 25,000, 30,000, 35,000, 40,000, 45,000, 50,000, 55,000, 60,000, 65,000, 70,000, 75,000, 80,000, 90,000 or 100,000 µg/L, and less than, less than about, up to, or up to about 5, 7, 10, 15, 20, 25, 30, 35, 40, 50, 75, 100, 200, 300, 400, 500, 700, 1000, 1500, 2000, 2500, 3000, 3500, 5000, 7000 or 10,000 mg/L.

Lithium Salts

The wood preservation compositions provided herein can further comprise one or more lithium salts. While not intending to be limited to the following, it is believed that the lithium salt contributes to the interaction between cellulose and the DMAc moiety of the surfactant or phospholipid such that the micelles or liposomes described herein can interact with wood cellulose. The type of lithium salt and the concentration thereof can be sufficient to cause the micelles or liposomes described herein to bind to wood cellulose, and can, in some embodiments, facilitate the infiltration of the micelles or liposomes provided herein into wood cells. Examples of lithium salts that can be used include, but are not limited to, LiF, LiCl, LiBr, LiI, LiOH, Li2CO3, LiHCO3, Li2NO3, Li2SO4, LiHSO4, Li3PO4, Li2HPO4, and LiH2PO4. The lithium salt can be present in aqueous dispersions containing the micelles or liposomes provided herein, and can be in a concentration from at least, at least about, greater than, or greater than about, 0.01, 0.02, 0.03, 0.05, 0.07, 0.1, 0.15, 0.2, 0.25, 0.3, 0.35, 0.4, 0.45, 0.5, 0.6, 0.7, 0.8, 0.9, 1, 1.2, 1.5, 2, 2.5, 3, 3.5, 5, 7, 10, 15, 20, or 25 µM, and less than, less than about, up to, or up to about 0.01, 0.02, 0.03, 0.05, 0.07, 0.1, 0.15, 0.2, 0.25, 0.3, 0.35, 0.4, 0.45, 0.5, 0.6, 0.7, 0.8, 0.9, 1, 1.2, 1.5, 2, 2.5, 3, 3.5, 5, 7, 10, 15, 20, or 25 mM.

Methods of Preserving Wood

In some embodiments, provided herein are methods of preserving wood, where the method includes (a) providing untreated wood; and (b) applying a wood preservative composition in accordance with the teachings provided herein to the untreated wood to produce treated wood. In the method, untreated wood is provided, where the untreated wood can include hardwood, lumber, or other wood for which the goal is the preservation thereof. The wood preservative composition can be delivered in liquid form, for example, in aqueous dispersion form, in accordance with aqueous dispersions provided herein.

In the methods of preserving wood provided herein the wood preservative composition is applied to the wood. The wood preservative composition can be applied to the wood using any of a variety of known methods for applying liquids to wood. Examples of methods include dipping the wood into a liquid, applying the liquid to the wood with a transfer roller, spraying the wood, liquid injection into the wood, slot-die-coating the wood, knife coating the wood, and any other known method for applying liquids to wood. In some embodiments, a method of applying the wood preservative composition is performed by a zero-pressure surface-coating method. In some embodiments, a method of applying the wood preservative composition is performed by pressure injection at low-pressure. Suitable pressures for the low-pressure liquid injection can be at least, at least about, more than, or more than about, 0.05, 0.1, 0.15, 0.2, 0.25, or 0.3 kg/mm$^2$. In some embodiments, the amount applied is up to, up to about, less than, or less than about, 1.0, 1.5, 2.0, 2.5, or 3.0 kg/mm$^2$. Furthermore, the above listing of lower and upper limits to pressures for the low-pressure liquid injection can be combined to create suitable ranges of pressures for the low-pressure liquid injection.

The quantity of wood preservative composition applied to the wood can be determined by the surface area of the wood to be treated. Thus, the quantity of wood preservative composition to be applied to the wood can be expressed in terms of unit area of wood. The amount of wood preservative composition applied is an amount sufficient to reduce susceptibility of the wood to decay in accordance with established standards known in the art. In some examples, up to, up to about, less than, or less than about 0.1, 0.2, 0.5, 1, 2, 3, 4, 5, 7, 10, 15, 20, 25, 30, 35, 40, 45, or 50 mg/cm$^2$ of the wood preservative composition is applied to the wood. Furthermore, the above listing of lower and upper limits to the amount of preservative applied to the wood can be combined to create suitable ranges of contemplated amounts of preservative applied to the wood.

The quantity of wood preservation compound applied to the wood can be determined by the surface area of the wood to be treated. Thus, the quantity of wood preservation compound to be applied to the wood can be expressed in terms of unit area of wood. The amount of wood preservation compound applied is an amount sufficient to reduce susceptibility of the wood to decay in accordance with established standards known in the art. In some examples, up to, up to about, less than, or less than about 1, 2, 5, 10, 20, 30, 40, 50, 70, 100, 150, 200, 250, 300, 350, 400, 450, or 500 µg/cm$^2$ of the wood preservative composition is applied to the wood. Furthermore, the above listing of lower and upper limits to the amount of preservative applied to the wood can be combined to create suitable ranges of contemplated amounts of preservative applied to the wood.

Pre-Treating Wood

In some embodiments, prior to application of the wood preservative composition provided herein to wood, the wood can be dried in order to enhance the application of the wood preservation composition. An example of such pre-treatment methods is drying the wood, which can provide a path for infiltrating a wood preservation solution such those provided herein. Pre-treatment also can be achieved by dissolving the cellulose of the wood using a cellulose-dissolving solvent or hydrolyzing the cellulose into low-molecular-weight compounds, and then dissolving the compounds in water. Various types of solvents, conventionally known as cellulose-dissolving solvents, can be used in a pre-treatment method.

In some embodiments, prior to applying the wood preservative composition provided herein to the wood, the wood is subjected to a heat treatment. In some embodiments, the heat treatment is conducted simultaneously with, or immediately prior to, applying the wood preservative composition to the wood in order to increase the benefit resultant from the heat treatment. In some embodiments, when wood is heat treated, improvement of efficiency of wood preservative composition application is expected because the pressure in the water-filled pits on the surface of wood is reduced, which results in enhanced permeation of the wood preservative composition into the pits.

Any of a variety of known methods can be used in the heat treatment of the wood including, but not limited to dry kiln treatment and wet bulb treatment. The temperature and duration of the heat treatment can vary depending on the type of heat treatment applied. For example, the heat treatment is applied in such a manner as to enhance permeation of liquids such as the wood preservative composition into the wood, but is not applied so as to substantially diminish the structural integrity of the wood. For a heat treatment such as kiln treatment, the heat treatment can be applied for at least, at least about, more than, or more than about, 30, 40, 50, 60, 70, 80 or 90 minutes at a temperature of at least, at least about, more than, or more than about, 60, 70, 80, 90, 100, 110, 120. In some embodiments, the heat treatment can be performed at a temperature that is less than, less than about, no more than, or no more than about 130, 140, 150, 160, 170, 180, 190, 200, or 250° C. The structural integrity of the wood can be assessed by determination of one or more structural properties including, but not limited to compression strength, bending strength, modulus of elasticity in bending, impact bending strength, radial-tangential swelling and shrinkage, and longitudinal swelling and shrinkage, using methods known in the art. In some embodiments of the methods provided herein, one or more of the structural properties of the wood after heat treatment is no less than, no less than about, more than, or more than about, 99, 98, 97, 95, 90, 85, 80, 75, 70, 60, or 50% of the corresponding structural property of the wood prior to the heat treatment.

In some embodiments that include a heat treatment, the heat treatment is performed immediately prior to applying the wood preservative composition to the untreated wood. For example, the wood preservative composition can be applied to the wood after heat treatment at least, at least about, no more than, or no more than about 15, 20, 25, 30, 45 or 60 minutes after the heat treatment.

Drying Wood

In some embodiments, after applying the wood preservative composition to the wood, the resultant pre-treated wood product can be dried.

Any of a variety of known methods can be used in the drying the wood including drying in a kiln, or drying under ambient conditions. The temperature and duration of the heat treatment can vary depending on the drying method applied. For example, the drying method may not substantially diminish the structural integrity of the wood. For a drying method such as kiln treatment, the drying can be performed for at least, at least about, more than, or more than about, 5, 10, 15, 20, or 30 minutes at a temperature of at least, at least about, more than, or more than about, 40, 45, 50, 60, 70, or 80° C. In some embodiments, the drying can be performed at a temperature that is less than, less than about, no more than, or no more than about 90, 100, 110, 120, or 150° C. The structural properties of the wood after drying in some cases may be no less than, no less than about, more than, or more than about, 99, 98, 97, 95, 90, 85, 80, 75, 70, 60, or 50% that of the wood prior to drying.

Wood Products Resultant from the Methods Provided Herein

Further contemplated herein are wood products resultant from any method provided herein. For example, wood products resultant from the methods provided herein include wood products that contain the wood preservative composition provided herein. In some embodiments of such wood products, at least, at least about, more than, or more than about 5, 7, 10, 15, 20, 25, 30, 35, 40, 45, or 50 µg/cm$^2$ of wood preservative composition is present in the wood product. For example, up to, up to about, less than, or less than about 500, 700, 1000, 1500, or 2000 µg/cm$^2$ of wood preservative composition is present in the wood product. In some embodiments, at least 50, 60, 70, 80, 90, 95, 97, or 99% of the wood preservative composition present in the wood product is at least 1 below the surface of the treated wood product within 1, 2, 3, 4, 5, 6, 7, 8, 9 or 10 hours of applying the wood preservative composition.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

Additional embodiments are disclosed in further detail in the following examples, which are not in any way intended to limit the scope of the claims.

Example 1

Preparation of a Surfactant Containing a DMAc Moiety and a Wood Preservative Composition Containing the DMAc-Modified Surfactant A surfactant that has a dimethylacetamide (DMAc) scaffold as its polar group is synthesized by reacting 2-amino-n,n-dimethylacetamide and stearoyl chloride, as shown in FIG. 1.

Figure 2:
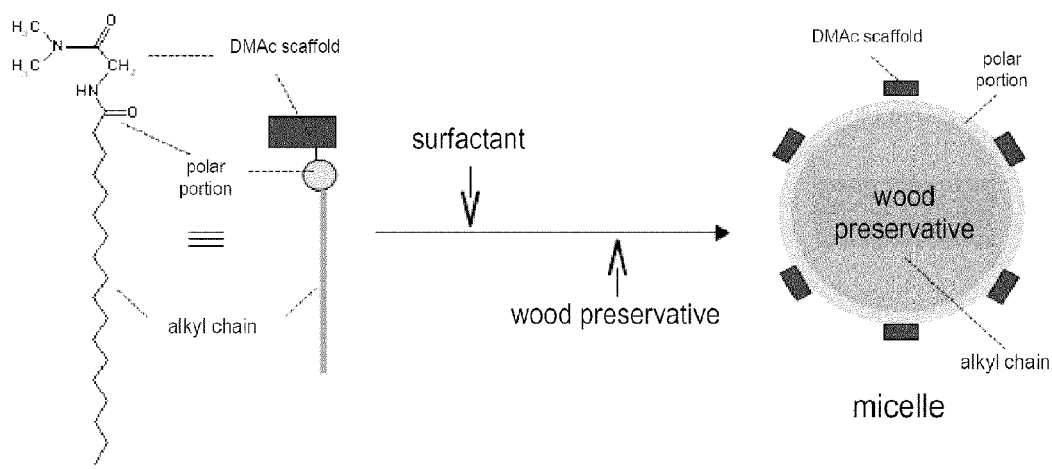
FIG. 2 depicts example steps that can be taken to prepare a micelle containing a wood preservative and a surfactant with a DMAc scaffold.

This DMAc surfactant and unmodified surfactant are mixed, and the mixture is further dispersed in water with a lipid-soluble wood preservative, thereby forming micelles containing the wood preservatives inside. By appropriately selecting a long alkyl chain length for the surfactant at this time, micelles of 10 to 50 nm diameter can be formed. A schematic of such a micelle is provided in FIG. 2. Finally, lithium chloride is added, thus completing the preparation of the wood preservative introducing agent.

Example 2

Figure 3:
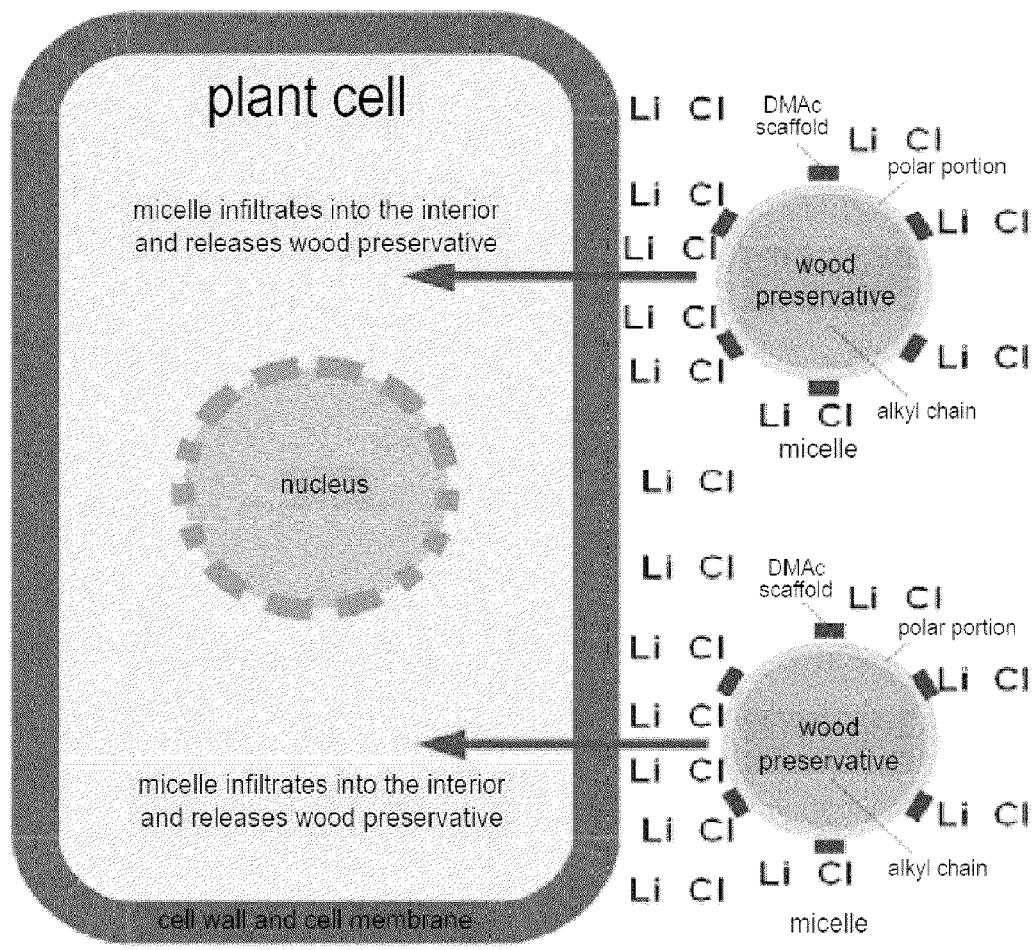
FIG. 3 depicts the infiltration of micelles containing a wood preservative and a surfactant with a DMAc scaffold into wood cells under conditions of high lithium concentration.

Aqueous Dispersion of a Wood Preservative Composition with High Lithium Chloride Concentration When the lithium chloride concentration is high (e.g., 10 mM), the micelles prepared according to Example 1 show a very high affinity with cell wall cellulose, and they are eventually taken into the cell walls. This is depicted in FIG. 3. The uptake results from numerous DMAc scaffolds at the micelle surfaces interact with the cell wall cellulose. These micelles pass through cell walls, not because they cleave molecular chains of cellulose, but because DMAc and lithium chloride break hydrogen bonds that are holding the molecular chains of cellulose in a similar manner to opening a zipper. Therefore, the cell walls return to their original state after the micelles infiltrate the cells. This is because the hydrogen bonds are easily reformed.

Example 3

Figure 4:
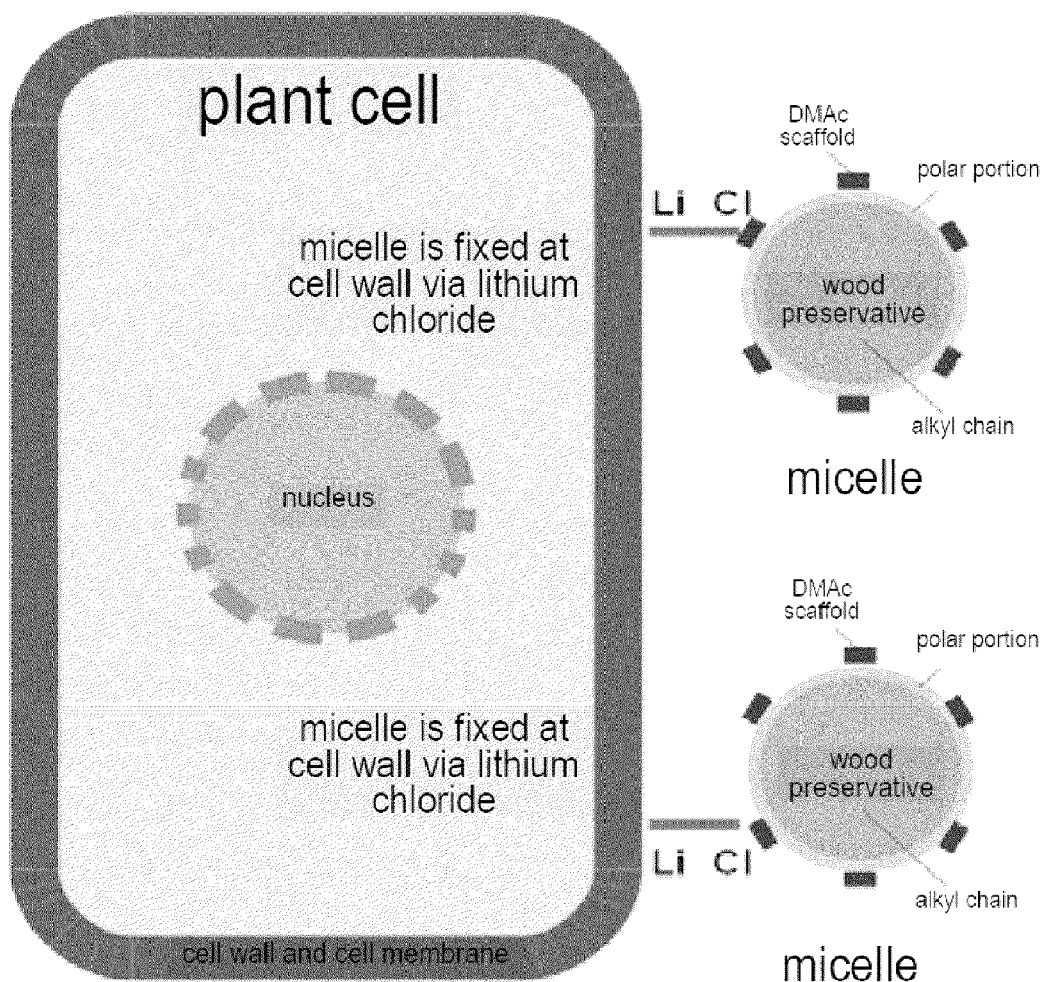
FIG. 4 depicts the infiltration of micelles containing a wood preservative and a surfactant with a DMAc scaffold into wood cells under conditions of low lithium concentration.

Aqueous Dispersion of a Wood Preservative Composition with Low Lithium Chloride Concentration When the lithium chloride concentration is low (e.g., 0.0001 mM), only a small portion of the DMAc at the surface of micelles prepared according to Example 1 maintains an affinity for cell wall cellulose. This is depicted in FIG. 4. When the water content of wood decreases after the completion of preservation treatment, the micelles become fixed at the cell wall surfaces via the lithium chloride.

After this, this wood is made commercially available for use, and, when the moist state of the wood slowly shifts to a dry state over time, the micelles eventually break down after 3 to 10 years to release the wood preservative held inside. Even if microbial invasion or a rapid increase in humidity occurs while slowly shifting to the dry state, the micelles release the wood preservative held inside because they cannot tolerate rapid changes in osmotic pressure.

Example 4

Preparation of a Surfactant Containing a Dmac Moiety and a Wood Preservative Composition Containing the DMAc-Modified Surfactant Synthesis of a phospholipid with an affinity for cellulose follows the surfactant synthesis described in Example 1, and liposome preparation is similar to the micelle preparation of Example 1.

An acid chloride precursor compound is formed in from 3-(dimethylcarbamoyl)propanoic acid. A phospholipid that has a DMAc scaffold as its polar group is synthesized by linking the acid chloride precursor compound to the amino group of phosphatydylserine. This DMAc-phospholipid and unmodified phospholipid are mixed, and the mixture is further dispersed in water with a water-soluble wood preservative, thereby forming liposomes containing the wood preservative in the internal aqueous phase. By applying ultrasonic waves at this time, single-layer liposomes of 30 to 60 nm diameter can be formed, whereas multi-layer liposomes of 0.1 to 0.5 µm diameter are formed if ultrasonic waves are not applied. Finally, lithium chloride is added to an external aqueous phase, thus completing the preparation of the wood preservative introducing agent.

Example 5

Aqueous Dispersion of a Wood Preservative Composition with High Lithium Chloride Concentration When the lithium chloride concentration is high (e.g., 10 mM), the liposomes of Example 4 show a very high affinity with cell wall cellulose, and they are eventually taken into the cell walls, similar to Example 2. The uptake results from numerous DMAc scaffolds at the liposome surfaces interact with the cell wall cellulose. These liposomes pass through cell walls, not because they cleave molecular chains of cellulose, but because DMAc and lithium chloride break hydrogen bonds that are holding the molecular chains of cellulose in a similar manner to opening a zipper. Therefore, the cell walls return to their original state after the liposomes infiltrate the cells. This is because the hydrogen bonds are easily reformed.

Example 6

Aqueous Dispersion of a Wood Preservative Composition with Low Lithium Chloride Concentration When the lithium chloride concentration is low (e.g., 0.0001 mM), only a small portion of the DMAc at the surface of micelles prepared according to Example 4 maintains an affinity for cell wall cellulose. When the water content of wood decreases after the completion of preservation treatment, the liposomes become fixed at the cell wall surfaces via the lithium chloride.

After this, this wood is made commercially available for use, and, when the moist state of the wood slowly shifts to a dry state over time, the liposomes eventually break down after 3 to 10 years to release the wood preservative held inside. Even if microbial invasion or a rapid increase in humidity occurs while slowly shifting to the dry state, the liposomes release the wood preservative held inside because they cannot tolerate rapid changes in osmotic pressure.

Examples 7-10

Additional Wood Preservative Compositions

Additional aqueous wood preservative compositions can be prepared in accordance with Examples 2 and 3 above, where the surfactants stearic acid (high lithium chloride: Example 7, low lithium chloride: Example 8), and lauric acid (high lithium chloride: Example 9, low lithium chloride: Example 10) can be used in the place of DMAc-stearoyl chloride.

Additional aqueous wood preservative compositions can be prepared in accordance with Examples 5 and 6 above, where the phospholipids phosphatidylcholine (high lithium chloride: Example 11, low lithium chloride: Example 12), and phosphatidylserine (high lithium chloride: Example 13, low lithium chloride: Example 14) can be used in the place of DMAc-phosphatydylserine.

Examples 15-26

Preservation of Wood

Untreated wood is treated with the aqueous wood preservative composition dispersion of Examples 2, 3, 5, 6, and 7-14 (Examples 15-26, respectively).

An untreated lumber of oak is provided. The untreated wood is subjected to heat treatment at a temperature of 80° C. for 180 minutes. The aqueous wood preservative composition dispersion is then applied to the dried wood by contacting the dried wood with the dispersion for 30 minutes at a temperature of 20-30° C. using a spray gun.

Oak lumber treated according to one or more of Examples 15-26 can be made commercially available for use, and, when the moist state of the wood slowly shifts to a dry state over time, the wood preservative is gradually released. Even if microbial invasion or a rapid increase in humidity occurs while slowly shifting to the dry state, the wood preservative is released upon change in osmotic pressure. In the case of microbial invasion, wood preservative is released and reduces or eliminates the microbial invasion, thus extending the life of the treated oak lumber. In contrast, untreated oak lumber is susceptible to microbial invasion, resulting in fungal invasion and accelerated decay of the lumber.

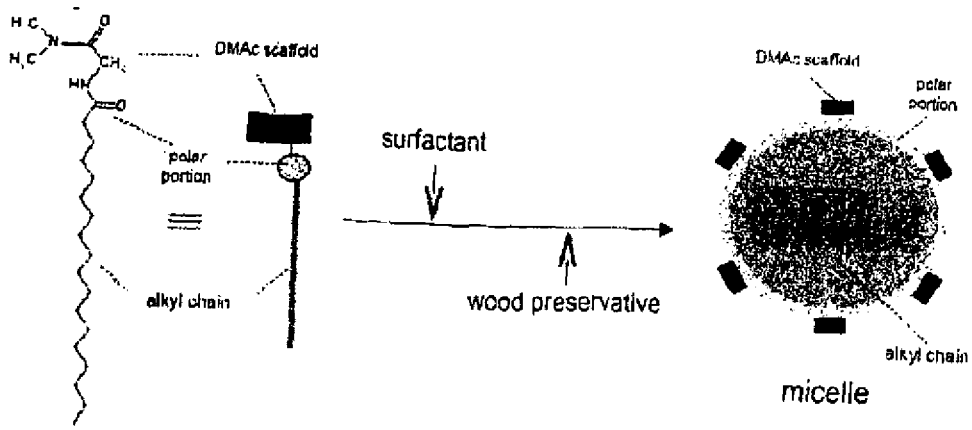

What is claimed is:

1. A wood preservative composition comprising:
   a micelle or liposome, wherein the micelle or liposome comprises at least one surfactant that comprises a 2-amino-N,N-dimethylacetamide (DMAc) moiety; and
   at least one wood preservative compound contained within the micelle or liposome; and
   at least one lithium salt.

2. The wood preservative composition of claim 1, wherein the wood preservative composition is in aqueous dispersion form.

3. The wood preservative composition of claim 2, wherein the concentration of the wood preservative composition in the aqueous dispersion is about 0.1 µM to about 10 mM.

4. The wood preservative composition of claim 1, wherein the at least one lithium salt is selected from LiF, LiCl, LiBr, LiI, LiOH, $Li_2CO_3$, $LiHCO_3$, $Li_2NO_3$, $LiSO_4$, $LiHSO_4$, $Li_3PO_4$, $Li_2HPO_4$ and $LiH_2PO_4$.

5. The wood preservative composition of claim 1, wherein the lithium salt is lithium chloride.

6. The wood preservative composition of claim 1, wherein the total amount of lithium salt present in the composition is about 0.1 µM to about 10 mM.

7. The wood preservative composition of claim 1, wherein the micelle or liposome further comprises at least one surfactant that does not contain a DMAc moiety.

8. The wood preservative composition of claim 1, wherein the wood preservative composition comprises micelles.

9. The wood preservative composition of claim 8, wherein the micelles have a mean diameter of about 10 nm to about 50 nm.

10. The wood preservative composition of claim 8, wherein the wood preservative compound is lipid, surfactant or soap soluble.

11. The wood preservative composition of claim 10, wherein the wood preservative compound is sodium dodecyl sulfate, sodium laureth sulfate, cetylpyridinium chloride, polyethoxylated tallow amine, cetyl alcohol, stearyl alcohol or combinations thereof.

12. The wood preservative composition of claim 1, wherein the wood preservative composition comprises unilamellar liposomes.

13. The wood preservative composition of claim 12, wherein the unilamellar liposomes have a mean diameter of about 30 nm to about 60 nm.

14. The wood preservative composition of claim 10, wherein the wood preservative compound is water soluble.

15. The wood preservative composition of claim 14, wherein the wood preservative compound is phosphatidylcholines, phosphatidylethanolamine, cholesterol, phosphatidylserine, phosphatidylinositol, or combinations thereof.

16. The wood preservative composition of claim 1, wherein the surfactant that comprises a DMAc moiety further comprises a $C_{8-50}$ alkyl moiety.

17. The wood preservative composition of claim 1, wherein the surfactant that comprises a DMAc moiety further comprises a phosphatidyl serine moiety.

18. The wood preservative composition of claim 1, wherein the surfactant that comprises a DMAc moiety is stearoyl-2-amino-N,N-dimethylacetamide, lauroyl-2-amino-N,N-dimethylacetamide, or a combination thereof.

19. The wood preservative composition of claim 1, wherein the amount of surfactant containing a DMAc moiety in the micelle or liposome is about 1% to about 95% (w/w) relative to the total amount of surfactant in the micelle or liposome.

20. The wood preservative composition of claim 1, wherein the amount of wood preservative compound contained in the wood preservative composition is about 70% to about 99% (w/w) relative to the total amount of the wood preservative composition.

21. A wood preservative composition comprising:
at least one surfactant that comprises a 2-amino-N,N-dimethylacetamide (DMAc) moiety;
at least one wood preservative compound;
an aqueous solvent; and
at least one lithium salt.

22. A preserved wood product comprising a wood product and the wood preservative composition of claim 1.

23. A method of preserving wood, the method comprising:
providing untreated wood; and
applying to the untreated wood the wood preservative composition of claim 1.

* * * * *

UNITED STATES PATENT AND TRADEMARK OFFICE
CERTIFICATE OF CORRECTION

Page 1 of 2

PATENT NO. : 8,889,262 B2
APPLICATION NO. : 13/878733
DATED : November 18, 2014
INVENTOR(S) : Mizusawa It is certified that error appears in the above-identified patent and that said Letters Patent is hereby corrected as shown below:

Delete Title Page, and replace with new Title Page. (Attached)

In the Specification

In Column 1, Lines 4-6, delete "This application is the U.S. National Phase under 35 U.S.C. §371 of International Application No. PCT/US2012/046937, filed Jul. 16, 2012." and insert
-- CROSS-REFERENCE TO RELATED APPLICATION
This application is the U.S. National stage filing under 35 U.S.C. §371 of International Application No. PCT/US2012/046937, filed Jul. 16, 2012, the entirety of which is hereby incorporated by reference. --, therefor.

In Column 5, Line 58, delete "palamitic" and insert -- palmitic --, therefor.

In Column 6, Line 25, delete "unlilamellar" and insert -- unilamellar --, therefor.

In the Claims

In Column 14, Line 46, in Claim 2, delete "in aqueous" and insert -- in an aqueous --, therefor.

Signed and Sealed this
Twenty-sixth Day of May, 2015

Michelle K. Lee
*Director of the United States Patent and Trademark Office*

(12) United States Patent
Mizusawa

(10) Patent No.: US 8,889,262 B2
(45) Date of Patent: Nov. 18, 2014

(54) METHODS AND SYSTEMS FOR DELIVERING WOOD PRESERVATIVES

(75) Inventor: Atsushi Mizusawa, Kyoto (JP)

(73) Assignee: Empire Technology Development LLC, Wilmington, DE (US)

(*) Notice: Subject to any disclaimer, the term of this patent is extended or adjusted under 35 U.S.C. 154(b) by 0 days.

(21) Appl. No.: 13/878,733

(22) PCT Filed: Jul. 16, 2012

(86) PCT No.: PCT/US2012/046937
§ 371 (c)(1),
(2), (4) Date: Apr. 10, 2013

(87) PCT Pub. No.: WO2014/014445
PCT Pub. Date: Jan. 23, 2014

(65) Prior Publication Data
US 2014/0017506 A1 Jan. 16, 2014

(51) Int. Cl.
B32B 23/04 (2006.01)

(52) U.S. Cl.
USPC ........ 428/532; 428/535; 428/536; 428/537.1; 427/397; 516/24; 514/354

(58) Field of Classification Search
USPC ............... 428/532, 535, 536, 537.1; 427/397; 516/24; 514/354
See application file for complete search history.

(56) References Cited

U.S. PATENT DOCUMENTS

| | | | |
|---|---|---|---|
| 4,115,313 A * | 9/1978 | Lyon et al. | 516/24 |
| 4,532,251 A * | 7/1985 | Spatz | 514/354 |
| 5,213,805 A * | 5/1993 | Wallach et al. | 424/450 |
| 2005/0255251 A1* | 11/2005 | Hodge et al. | 427/397 |

OTHER PUBLICATIONS

Keffer, J.L. "Motualevic Acids A-F . . ." Organic Letters 2009, 11;1087-1090.*
Vaca-Garcia, C. "Cellulose Esterification with Fatty Acids . . ." Journal of the American Oil Chemists Society, 1998, 75:315-319.*
Keffer, J.L. "Motualevic Acids A-F, Antimicrobial Acids from the Sponge Siliquariaspongia sp." Organic Letters 2009 11:1087-1090.
Vaca-Garcia, C. "Cellulose Esterification with Fatty Acids and Acetic Anhydride in Lithium Chloride/N,N-Dimethylacetamide Medium" Journal of the American Oil Chemists Society 1998 75:315-319.
International Search Report issued on the corresponding PCT Application No. PCT/US 12/46937, dated Sep. 21, 2012.
McCormick, C.L. "Solution Studies of Cellulose in Lithium Chloride and N,N-Dimethylacetamide" Macromolecules 1985 18:2394-2401.

* cited by examiner

Primary Examiner — Leszek Kiliman
(74) Attorney, Agent, or Firm — Knobbe Martens Olson & Bear LLP

(57) ABSTRACT

The present application relates to wood preservation, for example, surfactants and phospholipids for improving wood preservation. Included are surfactants and phospholipids containing a 2-amino-N,N-dimethylacetamide. Provided are wood preservative compositions containing these surfactants or phospholipids, methods of applying such wood preservative compositions to wood, and wood products resultant from some such methods. Also provided are wood products containing the wood preservative compositions provided herein.

23 Claims, 4 Drawing Sheets